US010345276B2

(12) United States Patent
Shreve et al.

(10) Patent No.: US 10,345,276 B2
(45) Date of Patent: Jul. 9, 2019

(54) PASSIVE COLUMN PRE-HEATER FOR USE IN CHROMATOGRAPHIC SYSTEMS

(71) Applicant: Waters Technologies Corporation, Milford, MA (US)

(72) Inventors: Joshua A. Shreve, Franklin, MA (US); Kurt D. Joudrey, Chelmsford, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 242 days.

(21) Appl. No.: 15/303,321

(22) PCT Filed: Apr. 10, 2015

(86) PCT No.: PCT/US2015/025293
§ 371 (c)(1),
(2) Date: Oct. 11, 2016

(87) PCT Pub. No.: WO2015/160650
PCT Pub. Date: Oct. 22, 2015

(65) Prior Publication Data
US 2017/0038345 A1    Feb. 9, 2017

Related U.S. Application Data

(60) Provisional application No. 61/979,140, filed on Apr. 14, 2014.

(51) Int. Cl.
*G01N 30/30*    (2006.01)
*G01N 1/44*    (2006.01)

(52) U.S. Cl.
CPC .............. *G01N 30/30* (2013.01); *G01N 1/44* (2013.01); *G01N 2030/3007* (2013.01)

(58) Field of Classification Search
CPC ........... G01N 30/30; G01N 2030/3007; G01N 2030/3015; G01N 2030/3046; G01N 1/44
(Continued)

(56) References Cited

U.S. PATENT DOCUMENTS 3,672,446 A    6/1972   Tibbetts et al.
4,404,845 A    9/1983   Schrenker
(Continued)

FOREIGN PATENT DOCUMENTS

WO    8103069 A1    10/1981
WO    8302006 A1    6/1983
(Continued)

OTHER PUBLICATIONS

Extended Search Report in European Patent Application No. 15779859.6, dated Nov. 2, 2017; 9 pages.
(Continued)

*Primary Examiner* — Robert R Raevis
(74) *Attorney, Agent, or Firm* — Schmeiser, Olsen & Watts LLP

(57) ABSTRACT

A passive pre-heater assembly includes a thermally conductive heat-spreading block and a plurality of passive pre-heaters in thermally conductive communication with the heat-spreading block. The plurality of the pre-heaters exchanges heat with the thermally conductive heat-spreading block. Each pre-heater includes a thermally conductive base in thermal communication with the heat-spreading block, and a plurality of thermally conductive fins is in thermal communication with the thermally conductive base. The plurality of fins of each pre-heater exchanges heat convectively with ambient air and conductively with the thermally conductive base of that pre-heater. A given one of the passive pre-heaters further comprises a tube in thermally conductive contact with the thermally conductive base of the (Continued)

given passive pre-heater. The thermally conductive heat-spreading block exchanges heat with a fluid passing through the tube of the given passive pre-heater.

30 Claims, 14 Drawing Sheets

(58) Field of Classification Search
USPC .......... 73/19.02, 23.25, 23.26, 23.35–23.42, 73/61.52, 61.53, 61.57, 61.59, 863.11, 73/863.12; 422/89, 90, 70; 210/656–659; 95/82–87; 96/101–107
See application file for complete search history.

(56) References Cited

U.S. PATENT DOCUMENTS

| | | | |
|---|---|---|---|
| 4,520,305 A | 5/1985 | Cauchy | |
| 6,799,629 B1 | 10/2004 | Cong et al. | |
| 7,177,152 B1 * | 2/2007 | Sun | F25B 21/02 165/104.33 |
| 2007/0181702 A1 | 8/2007 | Ziegler | |
| 2009/0211978 A1 | 8/2009 | Ognibene et al. | |
| 2012/0318782 A1 * | 12/2012 | Collins | H05B 1/00 219/441 |
| 2013/0052083 A1 | 2/2013 | Kirby et al. | |
| 2015/0196855 A1 * | 7/2015 | Waldbaur | B01D 15/12 210/198.1 |
| 2015/0377179 A1 * | 12/2015 | Nayar | F02G 1/053 60/517 |

FOREIGN PATENT DOCUMENTS

| | | |
|---|---|---|
| WO | 8302007 A1 | 6/1983 |
| WO | 2011085337 A1 | 7/2011 |

OTHER PUBLICATIONS

International Search Report & Written Opinion in counterpart International Patent Application No. PCT/US15/25293, dated Jul. 2, 2015; 9 pages.

International Preliminary Report on Patentability in counterpart International Patent Application No. PCT/US15/25293, dated Oct. 27, 2016; 8 pages.

* cited by examiner

PASSIVE COLUMN PRE-HEATER FOR USE IN CHROMATOGRAPHIC SYSTEMS

RELATED APPLICATION

This application claims the benefit of and priority to U.S. provisional application No. 61/979,140, filed Apr. 14, 2014, titled "Passive Column Pre-heater for use in Chromatographic Systems," the entirety of which application is incorporated by reference herein.

FIELD OF THE INVENTION

The invention relates generally to chromatography systems. More specifically, the invention relates to passive pre-heaters that pre-heat fluids before delivery to a chromatography separation column used in chromatography systems.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase comprised of a sample dissolved in a mixture of solvents (and/or other fluids), moves to a point of use, such as a separation column, referred to as the stationary phase. By passing the mobile phase through the column, the various components in the sample separate from each other at different rates and thus elute from the column at different times. A detector receives the separated components from the column and produces an output from which the identity and quantity of the analytes may be determined.

Temperature can influence the results of the analysis, affecting such properties as the separation performance of the column and the viscosity of a mobile phase. Therefore, maintaining an accurate constant column temperature is important to the accuracy and reproducibility of the results. The manner by which the column temperature is controlled is an important factor. Convective column-heating systems can produce dispersion because the direct flow of air onto the columns interacts with internal viscous heating to produce radial gradients. An alternative to convective column-heating systems are heated trough designs, for example, as disclosed in U.S. Pub. No. 2013/0052083, which is incorporated herein by reference. However, heated trough designs for long chromatography columns or series of columns can be expensive and a challenge to control.

In addition, accurate preheating of the fluid being delivered to the separation column can be critical to producing consistent retention times. If the temperature of the mobile phase supplied to the column is not constant, for example, for long (e.g., multi-hour) chromatographic runs where the variations in room temperature are significant, the accuracy of the chromatographic analysis can degrade. A device to pre-heat the mobile phase is sometimes used to reduce temperature fluctuations at the column inlet. However, existing active pre-heaters are known to have an offset error from the temperature set point. On the other hand, current methods of passive pre-heating that use conduction may not perform well in a convective system.

SUMMARY

All examples and features mentioned below can be combined in any technically possible way.

In one aspect, a passive pre-heater assembly comprises a thermally conductive heat-spreading block and a plurality of passive pre-heaters in thermally conductive communication with the heat-spreading block to exchange heat with the thermally conductive heat-spreading block. Each pre-heater comprises a thermally conductive base in thermal communication with the heat-spreading block and a plurality of thermally conductive fins in thermal communication with the thermally conductive base of the pre-heater. The plurality of fins is adapted to exchange heat convectively with ambient air and conductively with the thermally conductive base of the pre-heater. A given one of the passive pre-heaters further comprises a tube in thermally conductive contact with the thermally conductive base of the given passive pre-heater. The thermally conductive heat-spreading block exchanges heat with a fluid passing through the tube of the given passive pre-heater.

Embodiments of the passive pre-heater assembly may include one of the following features, or any combination thereof.

The given one of the passive pre-heaters may further comprise a groove formed in the thermally conductive base of the given passive pre-heater, and wherein the tube may be embedded within the tube, with an inlet end of the tube extending from one end of the groove, an outlet end of the tube extending from an opposite end of the groove, and the outlet end of the tube having a chromatography column fitting for coupling to a chromatography separation column. The tube may be secured within the groove by a thermal epoxy.

The passive pre-heater assembly may further comprise a thermal gasket disposed between the thermally conductive base of each pre-heater and the thermally conductive heat-spreading block. An edge of the heat-spreading block may have a mounting flange adapted to hold a temperature sensor.

The passive pre-heater assembly may further comprise a second thermally conductive heat-spreading block, and a second plurality of passive pre-heaters in thermally conductive communication with the second thermally conductive heat-spreading block to exchange heat therewith. Each pre-heater of the second plurality of passive pre-heaters may comprise a thermally conductive base in thermal communication with the second heat-spreading block, and a plurality of thermally conductive fins in thermal communication with the thermally conductive base of that pre-heater of the second plurality of passive pre-heaters. Each of the plurality of thermally conductive fins is adapted to exchange heat convectively with ambient air and conductively with the thermally conductive base of that pre-heater of the second plurality of passive pre-heaters. A given one of the second plurality of passive pre-heaters may further comprise a groove formed in the thermally conductive base of the given passive pre-heater of the second plurality of passive pre-heaters, and a tube embedded within the groove. A fluid passing through the tube of the given passive pre-heater of the second plurality of passive pre-heaters exchanges heat with the second thermally conductive heat-spreading block. The thermally conductive heat-spreading blocks may be in thermal communication with each other and may be integral portions of a single heat-spreading block.

The plurality of thermally conductive fins of each pre-heater of the second plurality of pre-heaters may extend in an opposite direction from the plurality of thermally conductive fins of each pre-heater of the other plurality of pre-heaters. A section of the second heat-spreading block may be spatially separated from and opposite of a corresponding section of the other heat-spreading block.

In another aspect, a passive pre-heater comprises a thermally conductive base and a plurality of parallel, thermally conductive fins in thermal communication with the thermally conductive base. The plurality of fins exchanges heat convectively with ambient air and conductively with the thermally conductive base. A tube is in thermally conductive contact with the thermally conductive base for effectuating an exchange of heat between the thermally conductive base and a fluid passing through the tube.

Embodiments of the passive pre-heater assembly may include one of the following features, or any combination thereof.

The thermally conductive base may have a groove formed therein, and the tube may be embedded within the groove. The tube may further comprise an inlet end extending from one end of the groove, and an outlet end extending from an opposite end of the groove, the outlet end of the tube having a chromatography column fitting for coupling to a chromatography separation column. The groove may be serpentine within the thermally conductive base. The tube may be secured within the groove by a thermal epoxy.

The passive pre-heater assembly may further comprise a cooling element thermally coupled to the thermally conductive base for cooling the thermally conductive base and effectuating an exchange of heat from the fluid passing through the tube in the groove and the thermally conductive base. Another embodiment of the pre-heater assembly may further comprise a thermal gasket disposed on the thermally conductive base covering the groove. The groove may be approximately two to three inches in length.

Further, the tube may have an inner diameter of approximately 0.005 inches. The thermally conductive base may have a width of approximately 1 inch and a height of approximately 2 inches.

In another aspect, a column-conditioning enclosure comprises a column chamber adapted to hold one or more chromatography separation columns and a passive pre-heater assembly. The passive pre-heater assembly comprises a thermally conductive heat-spreading block and a plurality of passive pre-heaters in thermally conductive communication with the heat-spreading block to exchange heat with the thermally conductive heat-spreading block. Each passive pre-heater comprises a thermally conductive base in thermal communication with the heat-spreading block and a plurality of thermally conductive fins in thermal communication with the thermally conductive base of the pre-heater. A given one of the passive pre-heaters further comprises a tube in thermally conductive contact with the thermally conductive base of the given passive pre-heater, with one end of the tube in fluidic communication with a given column of the one or more chromatography separation columns in the column chamber. The tube conveys a fluid to the given column. The column-conditioning enclosure further comprises an air mover moving a flow of air across the plurality of thermally conductive fins of each of the passive pre-heaters, wherein (i) each of plurality of thermally conductive fins exchanges heat convectively with the flow of air and conductively with the thermally conductive base of that pre-heater, (ii) the thermally conductive base of each passive pre-heater exchanges heat conductively with the heat-spreading block, and (iii) the heat-spreading block exchanges heat conductively with the fluid conveyed by the tube.

Embodiments of the column-conditioning enclosure may include one of the following features, or any combination thereof.

The column-conditioning enclosure may further comprise a shelf disposed near the heat-spreading block to contain the flow of air near the plurality of thermally conductive fins of the plurality of passive pre-heaters. The plurality of thermally conductive fins of each passive pre-heater may be aerodynamically oriented with a direction of the flow of air.

The column-conditioning enclosure may further comprise a sliding rail coupled to the passive pre-heater assembly. The sliding rail is adapted to slide into and out of the enclosure with the passive pre-heater assembly coupled thereto. An edge of the heat-spreading block may have one or mounting flanges adapted to slidably couple the heat-spreading block to the sliding rail. An edge of the heat-spreading block may have a mounting flange adapted to hold a temperature sensor.

The column-conditioning enclosure may further comprise a thermal gasket disposed between the thermally conductive base of each pre-heater and the thermally conductive heat-spreading block.

Other embodiments of the column-conditioning enclosure may further comprise a second thermally conductive heat-spreading block, and a second plurality of passive pre-heaters in thermally conductive communication with the second heat-spreading block to exchange heat therewith. Each pre-heater of the second plurality of passive pre-heaters may comprise a thermally conductive base in thermal communication with the second heat-spreading block, and a plurality of thermally conductive fins in thermal communication with the thermally conductive base of the pre-heater. Each of the plurality of thermally conductive fins may be adapted to exchange heat convectively with the flow of air and conductively with the thermally conductive base of that pre-heater of the second plurality of passive pre-heaters. A given pre-heater of the second plurality of passive pre-heaters may further comprise a groove formed in the thermally conductive base of the given passive pre-heater of the second plurality of passive pre-heaters, and a tube embedded within that groove, one end of the tube being in fluidic communication with a second given column of the one or more chromatography separation columns in the column chamber. The tube conveys a fluid to the second given column, wherein (i) each of plurality of thermally conductive fins of the second plurality of pre-heaters exchanges heat convectively with the flow of air and conductively with the thermally conductive base of that pre-heater, (ii) the thermally conductive base of each of the second plurality of passive pre-heaters exchanges heat conductively with the second heat-spreading block, and (iii) the second heat-spreading block exchanges heat conductively with the fluid conveyed by the tube in the groove of the given pre-heater of the second plurality of passive pre-heaters.

The thermally conductive heat-spreading blocks may be in thermal communication with each other and may be integral portions of a single heat-spreading block. The plurality of thermally conductive fins of each pre-heater of the second plurality of pre-heaters may extend in an opposite direction from the plurality of thermally conductive fins of each pre-heater of the other plurality of pre-heaters. A section of the second heat-spreading block may be spatially separated from and opposite of a corresponding section of the other heat-spreading block.

In another aspect, the invention features a method for pre-heating a fluid being delivered to a chromatography separation column. The method comprises thermally coupling a plurality of passive pre-heaters to a thermally conductive heat-spreading block, configuring a given pre-heater of the plurality of passive pre-heaters with a tube and a column fitting for conveying a fluid to a chromatography separation column, convectively transferring heat from ambient air to each pre-heater of the plurality of passive pre-heaters, conductively transferring heat from each of the plurality of passive pre-heaters to the thermally conductive heat-spreading block, and conductively transferring heat from the heat-spreading block to the fluid passing through the tube in the given pre-heater of the passive pre-heaters.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Column-conditioning systems described herein are convective systems that achieve near-adiabatic conditions for a column chamber having one or more chromatography separation columns installed within. The column-conditioning systems employ a duct system that distributes a heated airflow without directly blowing air onto the one or more columns because the column chamber is isolated from the airflow. The heated airflow circulates through the duct system around the column chamber, heating the column chamber walls, which radiate heat to the one or more columns installed within the column chamber. A ducted door of the column-conditioning system is part of the duct system, which, when open, enables access to the column chamber for installing and removing columns, and which, when closed, completes the circulatory loop of the duct system.

Passive pre-heaters can be disposed in the path of the heated airflow to heat the fluid entering into the columns. By convective and conductive means, the passive pre-heaters transfer heat from the ambient air to fluids passing through tubes thermally coupled to the pre-heaters. Alternatively, a pre-heater can be configured with a cooling element, such as a thermoelectric device, to cool a fluid being delivered to a column.

Passive pre-heater assemblies described herein include one or more passive pre-heaters adapted to exchange heat convectively with the ambient air. Each pre-heater has a thermally conductive base with a groove formed therein. The groove in the thermally conductive base holds a tube with a chromatography column fitting at one end for coupling to a chromatography separation column and through which to deliver a fluid to the column. Alternatively, the tube can be cast in the thermally conductive base. The fluid exchanges heat with the thermally conductive base as the fluid passes through the tube. A plurality of thermally conductive fins is in thermal communication with the thermally conductive base. The fins conduct heat, acquired convectively from the ambient air, to the thermally conductive base; and from the base, the heat transfers conductively to the fluid in the tube. Alternatively, the fins can conduct heat from the thermally conductive base and convectively transfer the heat to the ambient air. The passive pre-heater assemblies can include a thermally conductive heat-spreading block onto which multiple pre-heaters are mounted. The heat-spreading block distributes the heat load among all the pre-heaters.

Figure 1:
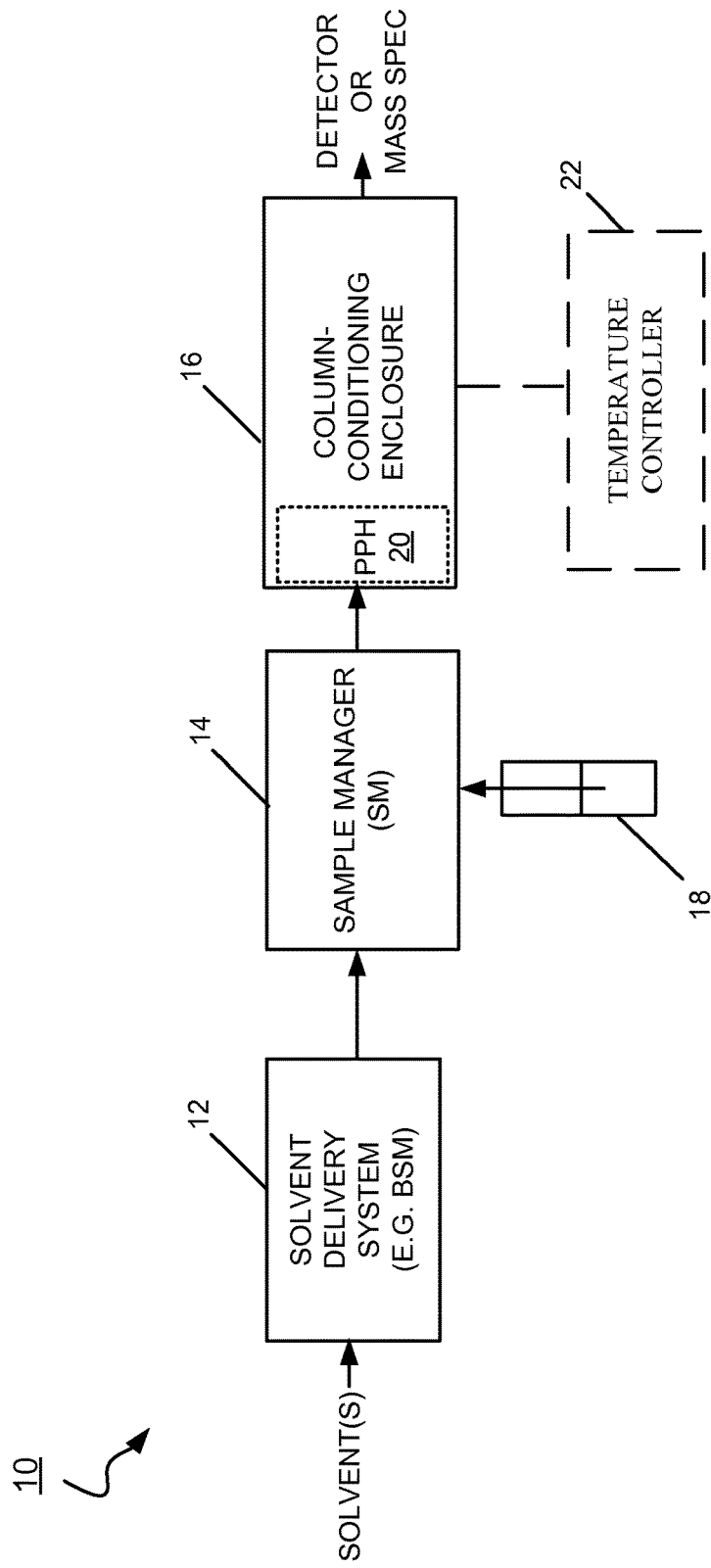
FIG. 1 is a block diagram of an embodiment of a chromatography system including a column-conditioning enclosure.

FIG. 1 shows an embodiment of a chromatography system 10 for separating a sample into its constituents. The chromatography system 10 includes a solvent delivery system 12 in fluidic communication with a sample manager 14. Generally, the solvent delivery system 12 includes pumps (not shown) in fluidic communication with solvent reservoirs from which the pumps draw solvents. The solvent delivery system 12 delivers a mixture of solvents (e.g., $CO_2$) to the sample manager 14. The sample manager 14 is in fluidic communication with a sample source 18 from which the sample manager acquires and introduces a sample to the solvent mixture arriving from the solvent delivery system 12.

In fluidic communication with the sample manager 14 is a column-conditioning enclosure 16 (also referred to as an oven) for receiving therefrom the solvent composition containing the sample. The column-conditioning enclosure 16 provides a controlled temperature environment for one or more chromatography separation columns used in separating sample-solvent compositions. Each separation column is adapted to separate the various components (or analytes) of the sample from each other as the mobile passes through, and to elute the analytes (still carried by the mobile phase)

from the column at different times. Embodiments of the separation column include a variety of sizes (e.g., preparative, semi-preparative, analytical, or capillary-scale packed-bed columns or open tubular columns) and a variety of preparations (e.g., in conventional metallic, fused silica, or polymeric tubes, or in metallic, ceramic, silica, glass, or polymeric microfluidic platforms or substrates of various IDs). The lengths of some columns installed in the column-conditioning enclosure 16, individually or connected in series, can be between two to three feet long.

As described further below, the column-conditioning enclosure 16 can optionally include a passive pre-heater assembly 20 for controlling the temperature of the fluidic sample composition before it enters a column. In general, the pre-heater assembly 20 causes the temperature of the fluidic sample to match approximately the air temperature around the column. "Passive" herein means without an active temperature control. The pre-heater assembly 20 is referred to as "passive" in that the pre-heater assembly 20 achieves a transfer of heat from ambient air to the fluid without any active temperature control on the part of the pre-heater assembly 20. Notwithstanding its "passive pre-heater assembly" name, some embodiments of the passive pre-heater assembly 20 may include actively controlled cooling elements by which to cool the fluid. To encompass such embodiments of pre-heater assemblies with cooling capabilities, the passive pre-heater assembly 20 may be referred to as a fluid thermal conditioner. From the column-conditioning enclosure 16, the constituents of the separated sample pass to a detector or other equipment, for example, a mass spectrometer, or a Flame Ionization Detector (FID), for analyzing the separation.

A temperature controller 22 can be in communication with the column-conditioning enclosure 16 to determine the current temperature of the controlled temperature environment based on one or more temperature sensors disposed within the column-conditioning enclosure 16 and, if necessary, to adjust the temperature produced by the column-conditioning enclosure 16 in order to attain a target air temperature. A computing system (not shown) with a processor programmed to set, monitor, and adjust, if necessary, the temperature can be used to implement the temperature controller 22.

Figure 2:
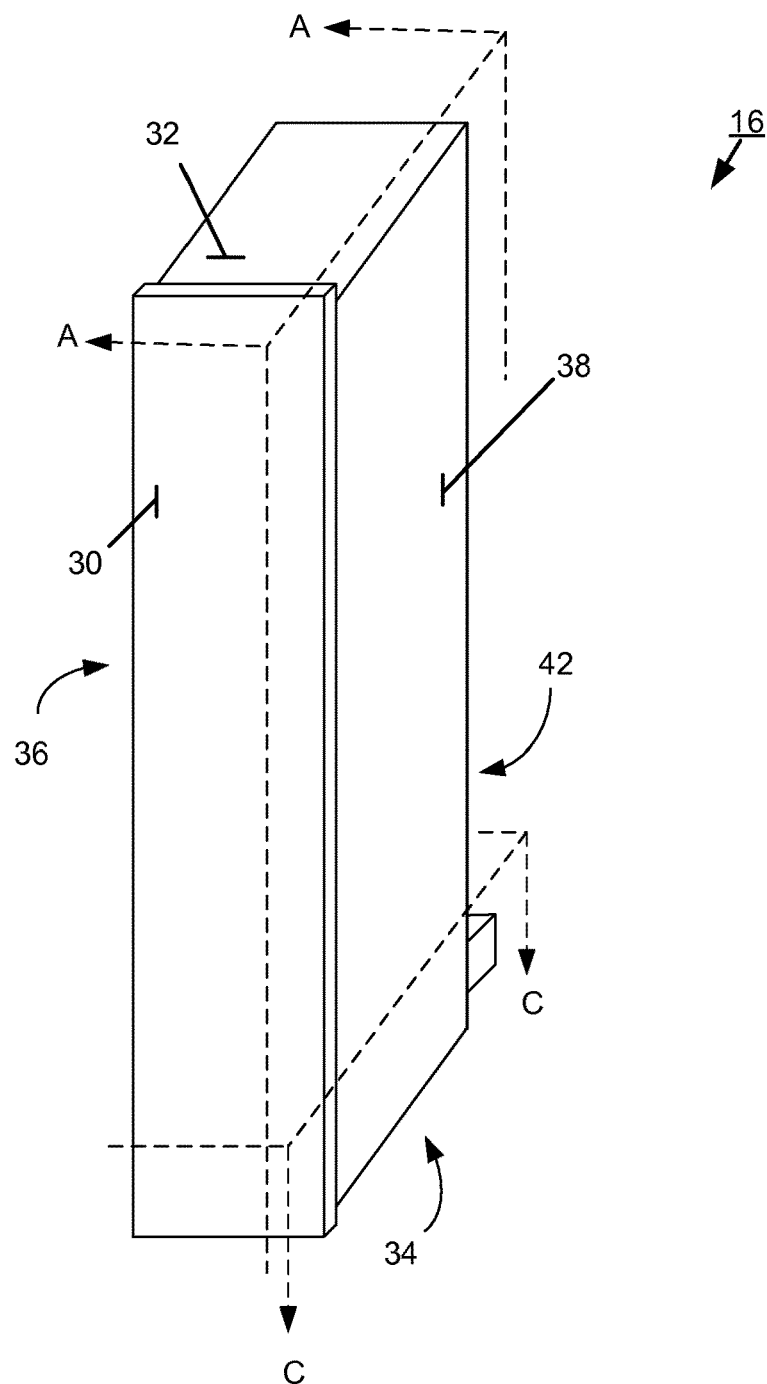
FIG. 2 is an isometric front view of an embodiment of the column-conditioning enclosure.

FIG. 2 shows an embodiment of the column-conditioning enclosure 16 with a front door 30, a top 32, a bottom 34, left and right sides 36, 38, and a rear side 42. It is to be understood that such terms as left, right, top, bottom, front, and rear are relative terms used for purposes of simplifying the description of features of the enclosure as shown in the figures, and are not used to impose any limitation on the structure of the enclosure itself. In this embodiment, the front door 30 is hinged along the left side 36 of the column-conditioning enclosure 16.

Figure 3:
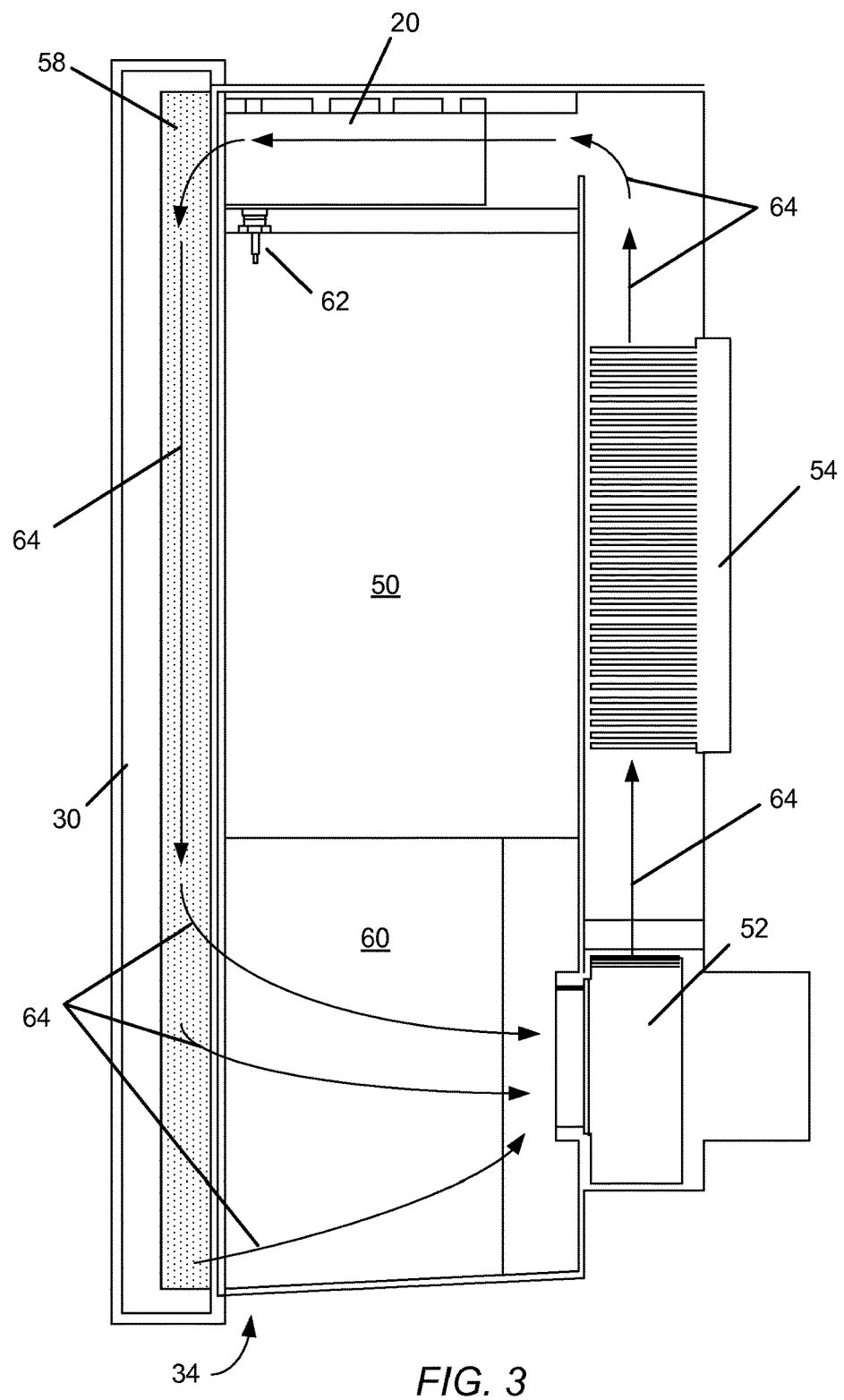
FIG. 3 is a cross-sectional view of the column-conditioning enclosure of FIG. 2.
Figure 7:
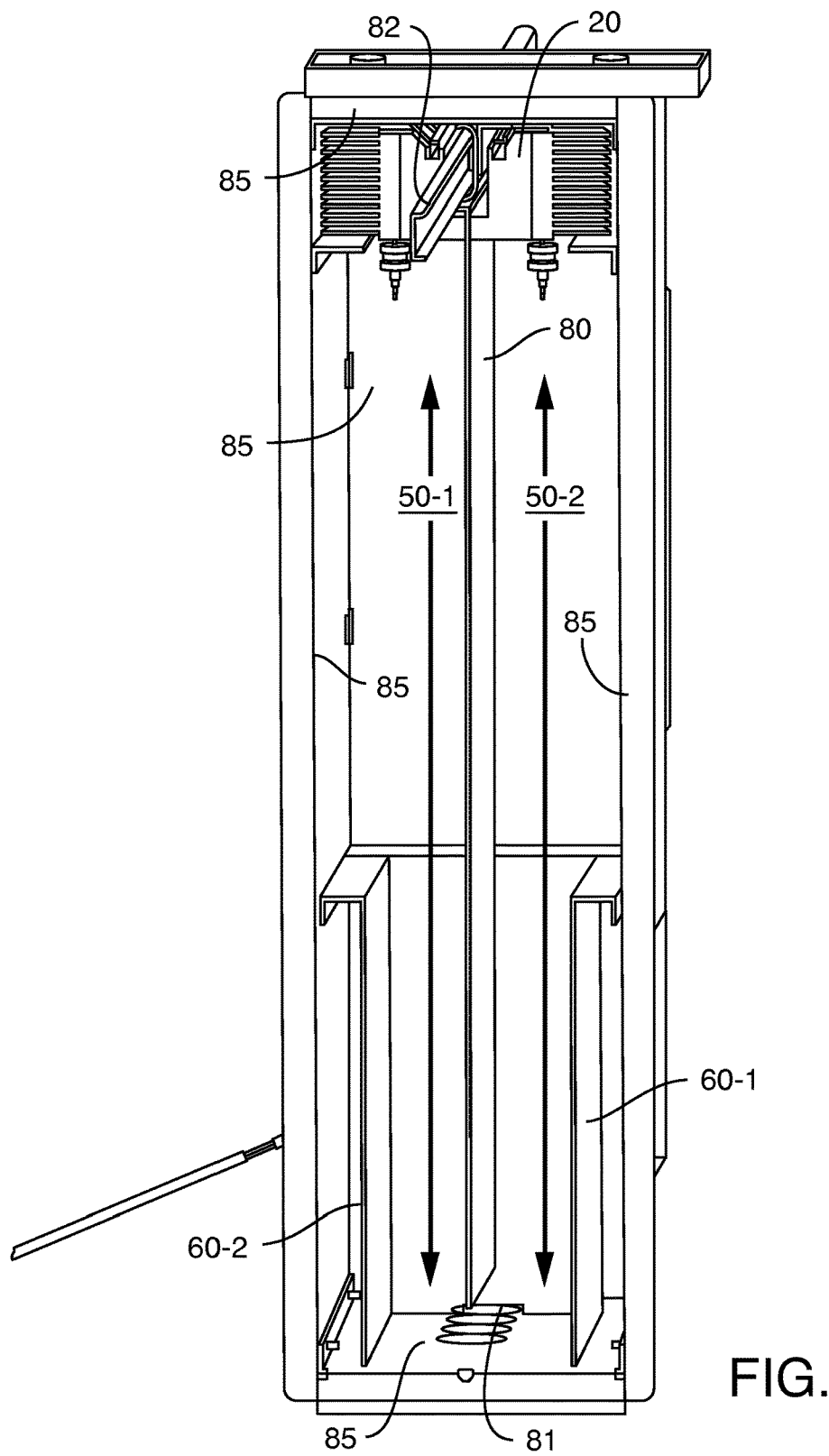
FIG. 7 is a front view of the column-conditioning enclosure with the door removed to expose an interior column chamber and return plenum that passes on opposite sides of the column chamber.

FIG. 3 shows a cross-section of the column-conditioning enclosure 16 along the line A-A in FIG. 2. The column-conditioning enclosure 16 includes a chromatography column chamber 50, an air mover 52, an actively controlled heat exchanger system 54, the passive pre-heater assembly 20, the front door 30 with an internal duct 58 extending therethrough from top to bottom, and a return plenum 60. The chromatography column chamber 50 extends down between side ducts of the return plenum 60, as illustrated in FIG. 7. The return plenum 60 can be made of sheet metal.

The passive pre-heater assembly 20 (or fluid thermal conditioner) includes a fitting 62 for connecting to a chromatography column (not shown) within the column chamber 50. The passive pre-heater assembly 20 and the column chamber 50 can be adapted to support multiple columns, connected in series, in parallel, or both. For example, a WATERS® UltraPerformance Convergence Chromatography (UPC$^2$®) system can have 8 columns in parallel; whereas a WATERS® ACQUITY® Advanced Polymer Chromatography™ (APC™) system can have one or two banks of columns configured in series (both types of chromatography systems are produced by Waters Corporation of Milford, Mass.). The passive pre-heater assembly 20 and the column chamber 50 can also be adapted to support H-Class systems.

Arrows 64 show generally the path taken by air circulating through a system of ducts around the chromatography column chamber 50. The air mover 52 produces and directs a flow of air to the actively controlled heat exchanger system 54. The airflow passes through the actively controlled heat exchanger system 54, which transfers heat to the airflow by convection. The heated air passes next through the passive pre-heater assembly 20. The pre-heater assembly 20 is the first subsystem after the heat exchanger system 54 so that the flowing air is at its hottest when it reaches the passive pre-heater assembly 20. The airflow then moves down through the interior duct 58 in the front door 30, and then out of the front door 30 through the lower ducts (FIG. 4) into the return plenum 60. The airflow passes through the return plenum 60 around the inner column chamber 50 and back to the air mover 52. The duct system thus circulates a heated airflow that heats the chamber walls. Heat radiates from the chamber walls to heat the columns in the column chamber 50, without air blowing directly on the columns. Accordingly, the column chamber 50 provides a near-adiabatic environment for the columns when the oven is at steady state because there is minimal airflow into and within the chamber 50.

Although described herein predominantly in the context of heating the airflow circulating through the duct system, other embodiments of the heat exchanger system 54 can operate to cool the circulating airflow. Examples of devices for implementing the heat exchanger system 54 as a cooling system include, but are not limited to, thermoelectric devices and refrigeration units. The airflow passes through the actively controlled heat exchanger system 54, which draws heat from the airflow. The cooled air passes next to the fluid thermal conditioner (i.e., passive pre-heater assembly) 20. The cooled airflow then moves down through the interior duct 58 in the front door 30, and then out of the front door 30 through the lower ducts (FIG. 4) into the return plenum 60. The airflow passes through the return plenum 60 around the inner column chamber 50 and back to the air mover 52. The duct system thus circulates a cooled airflow that cools the column chamber 50 and, thereby, each column within the column chamber, without air blowing directly on the columns.

Figure 4:
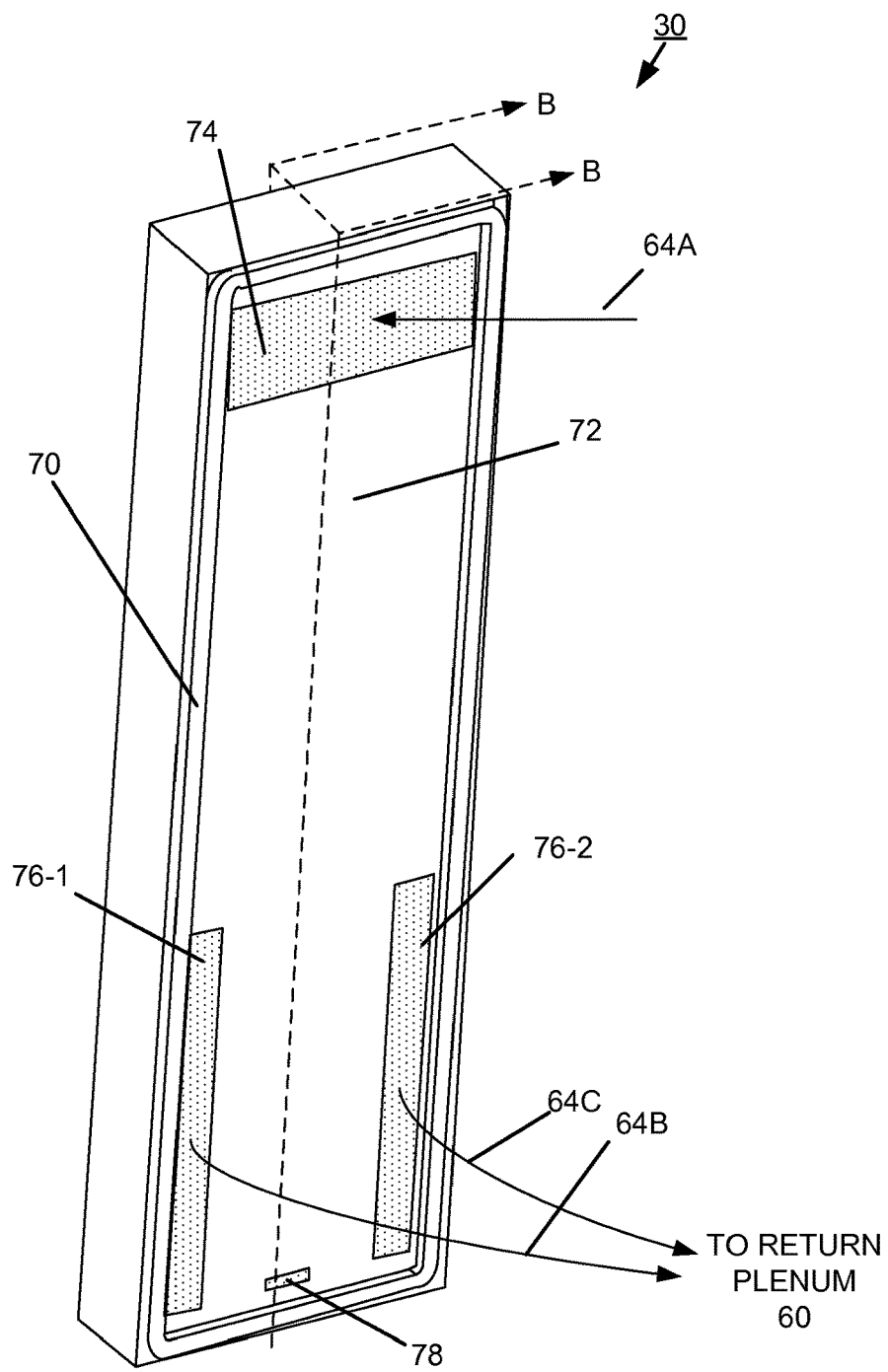
FIG. 4 is an inside view of a ducted front door of the column-conditioning enclosure.
Figure 5:
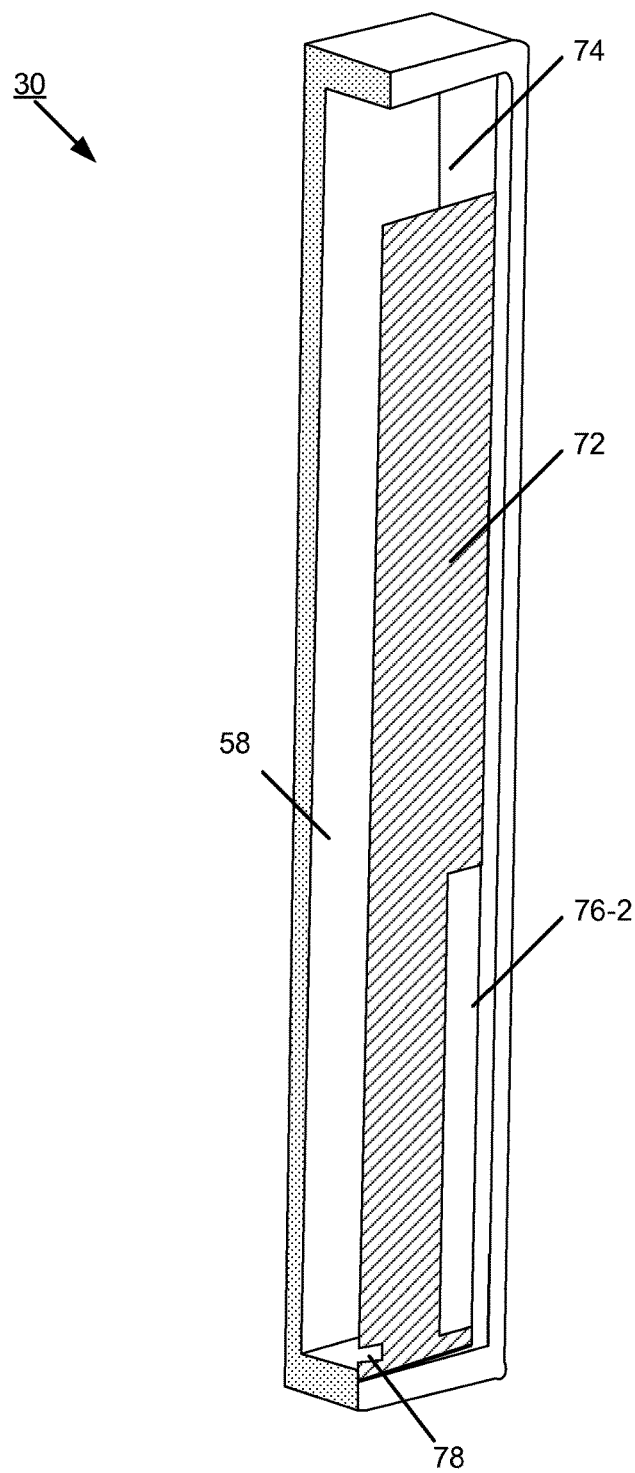
FIG. 5 is a cross-sectional view of inside view of the front door of FIG. 4.

FIG. 4 shows an inside view of the front door 30. Around the periphery of the door 30 is a thermal gasket 70 that seals the column-conditioning enclosure 16 when the front door 30 is closed shut. The door 30 has an interior panel 72 with a horizontal upper slot 74, two lower vertical slots 76-1, 76-2 (generally, 76), and a bottom horizontal slot 78. Air flows into the duct 58 through the horizontal upper slot 74 (arrow 64A) and exits the duct 58 through the two lower vertical slots 76-1, 76-2 (arrows 64B, 64C, respectively) and the bottom horizontal slot 78. The bottom horizontal slot 78 facilitates sweeping solvent vapors off the floor of the column chamber 50. The interior panel 72 can be thermally insulated to keep the column chamber 50 from losing heat when heated to a desired temperature or from gaining heat when cooled to a desired temperature FIG. 5 shows a cross-section of the inside view of the front door 30 along the line B-B in FIG. 4. The cross-section shows the interior duct 58 extending generally through the length and width of the front door 30.

Figure 6:
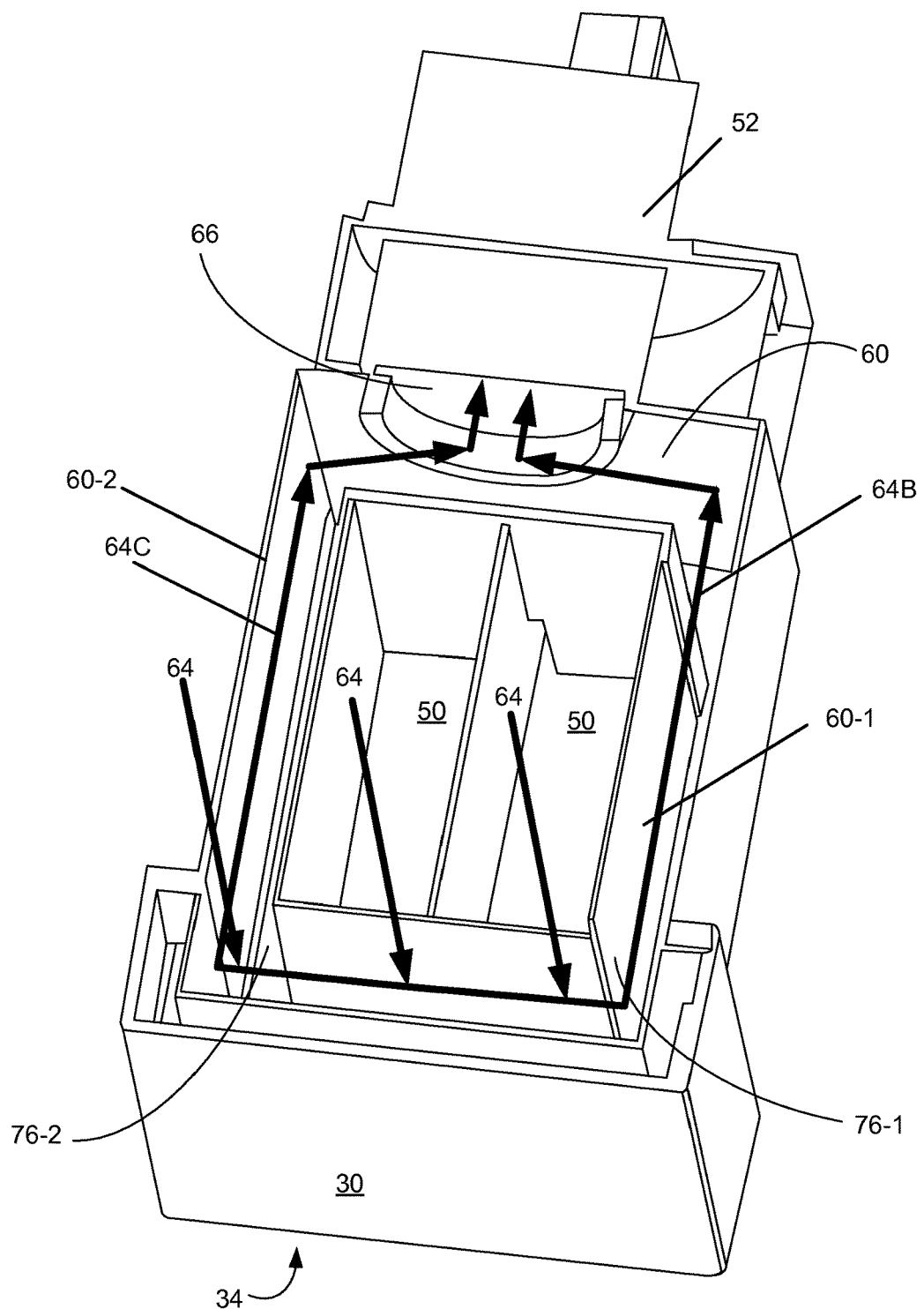
FIG. 6 is another cross-sectional view of the column-conditioning enclosure of FIG. 2, showing the bottom of the enclosure.

FIG. 6 shows a cross-section of the column-conditioning enclosure 16 along the line C-C in FIG. 2, showing the enclosure bottom 34. The airflow, as indicated by arrows 64, passes down through the internal duct 58 (FIG. 3) in the front door 30. The airflow 64 exits the duct 58 through vertical door slots 76-1, 76-2, dividing into two airflow paths 64B, 64C through two side ducts 60-1, 60-2 of the return plenum 60. The two airflow paths 64B, 64C pass through the two side ducts 60-1, 60-2 on opposite sides of the column chamber 50 and come together at the intake 66 of the air mover 52.

FIG. 7 shows a front view of the column-conditioning enclosure 16 with the front door 30 removed to expose the interior column chamber 50 and the return plenum 60 that passes on opposite sides of the column chamber 50. Each side duct 60-1, 60-2 of the return plenum 60 aligns with one of the vertical exit slots 76-1, 76-2 (FIG. 5) in the front door 30. A central panel 80 vertically divides the column chamber 50 into two column sub-compartments 50-1, 50-2. A horizontal slot 81 aligns with the horizontal exit slot 78 of the front door 30 (a duct 83 (FIG. 8) runs between the slots 78, 81, to keep the column chamber 50 isolated from the airflow). At the top of the column-conditioning enclosure 16 is the pre-heater assembly 20 slidably mounted onto a sliding rail 82. Accordingly, the pre-heater assembly 20 can slide into and out of the top of the column-conditioning enclosure 16 (with the front door open), to facilitate access thereto. The walls 85 defining the column chamber 50, which include the panels of the side ducts 60-1, 60-2, the base, top, and rear of the enclosure 16, and the interior panel 72 of the door 30 when closed, can be made of thermally conductive material (e.g., sheet metal), of a non-thermally conductive material (e.g., plastic, foam), or of any combination thereof.

Figure 8:
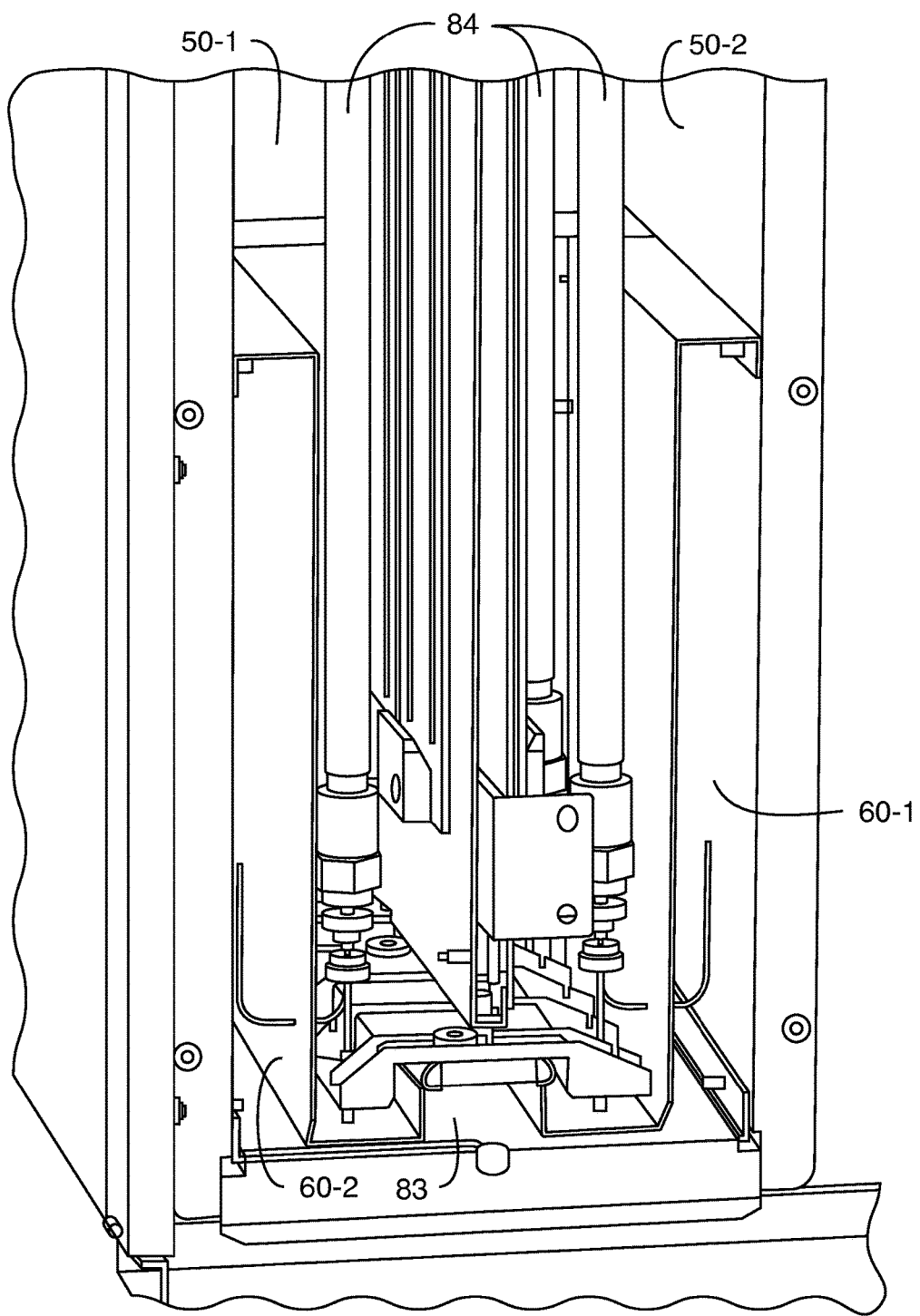
FIG. 8 is a front view of the lower section of the column-conditioning enclosure with the door removed to expose the interior column chamber configured with a plurality of columns.

FIG. 8 shows a front view of the lower section of the column-conditioning enclosure 16 with the front door 30 removed to expose the interior column chamber 50 configured with a plurality of columns 84. For illustration purposes, one column 84 is installed in sub-compartment 50-1, and two columns 84 are installed in sub-compartment 50-2. The removal of the front door also exposes the open ends of the side ducts 60-1, 60-2 and the open end of the bottom duct 83 that runs below the column chamber 50.

Figure 9:
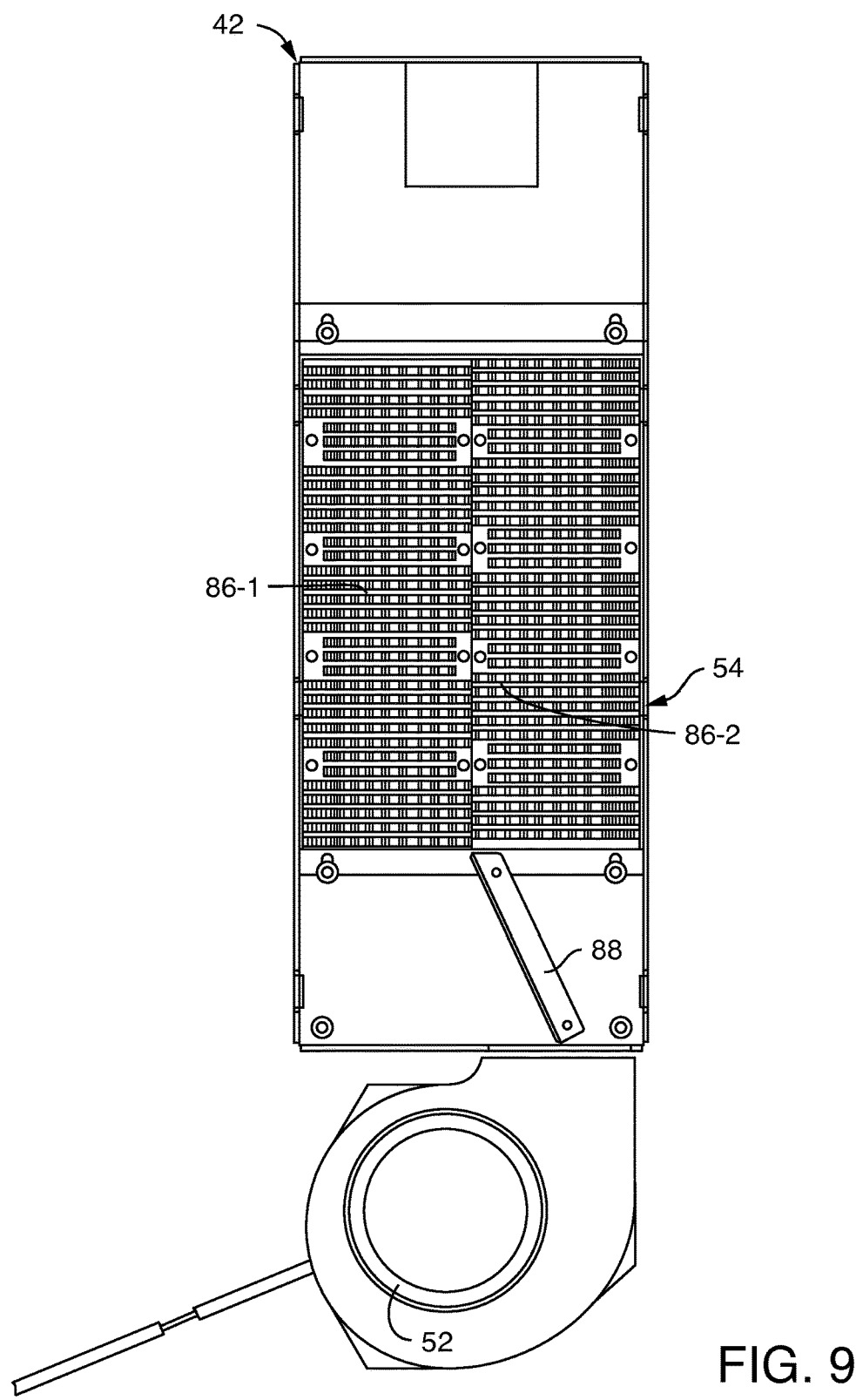
FIG. 9 is a front view of the rear panel of the column-conditioning enclosure with an air mover disposed adjacent to an actively controlled heat exchanger system.

FIG. 9 shows a front view of the rear panel 42 with the air mover 52 disposed adjacent to the actively controlled heat exchanger system 54. Embodiments of the air mover 52 include, but are not limited to, a blower and a fan. Advantageously, the motor of the air mover 52 can be external to the enclosure 16, thereby reducing the likelihood of an undesirable ignition of vapor by the running motor. This disclosed embodiment of the actively controlled heat exchanger system 54 includes a pair of active heaters 86-1, 86-2 (generally, 86). An air guide 88 divides and guides the air blown by the air mover 52 across each of the active heaters 86.

Figure 10:
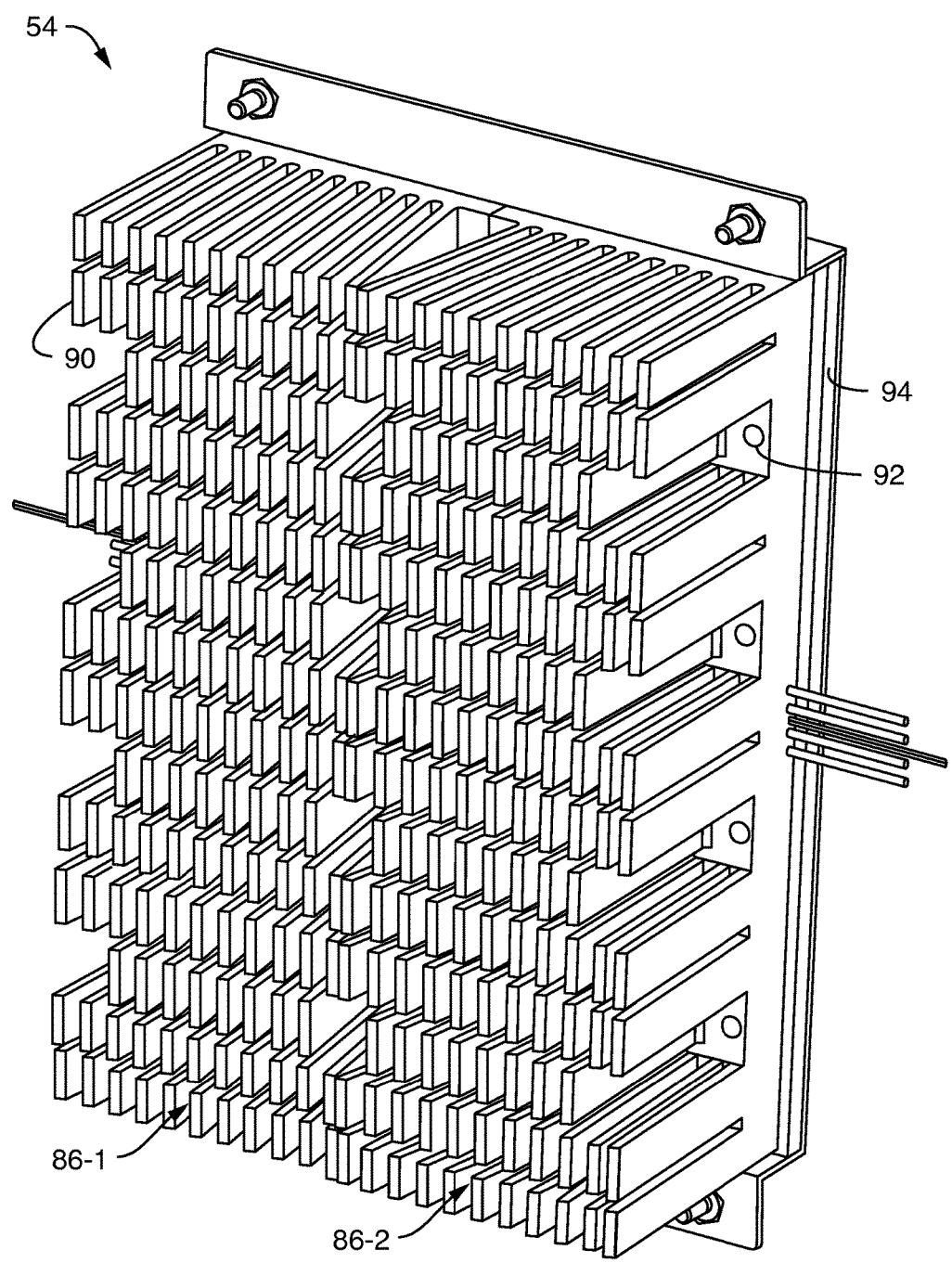
FIG. 10 is a front view of the actively controlled heat exchanger system including the pair of actively controlled heaters.

FIG. 10 shows a front view of an embodiment of the actively controlled heat exchanger system 54 including the pair of actively controlled heaters 86-1, 86-2. Each heater 86 is comprised of an array of thermally conductive fins 90 arranged in columns and rows. Although this embodiment of actively controlled heat exchanger system has two heaters 86, other embodiments can have as few as one active heater or more than two active heaters. Through-holes 92 provide access to fasteners that mount the front side of the actively controlled heat exchanger system 54 to a rear plate 94. Some fins 90 are missing from the array to allow access to these through-holes 92. When installed in the enclosure 16, the rear plate 94 of the heat exchanger system 54 is isolated from the column chamber 50. In one embodiment, the actively controlled heat exchanger system 54 attains and maintains the temperature of the air at 90° C.

Figure 11:
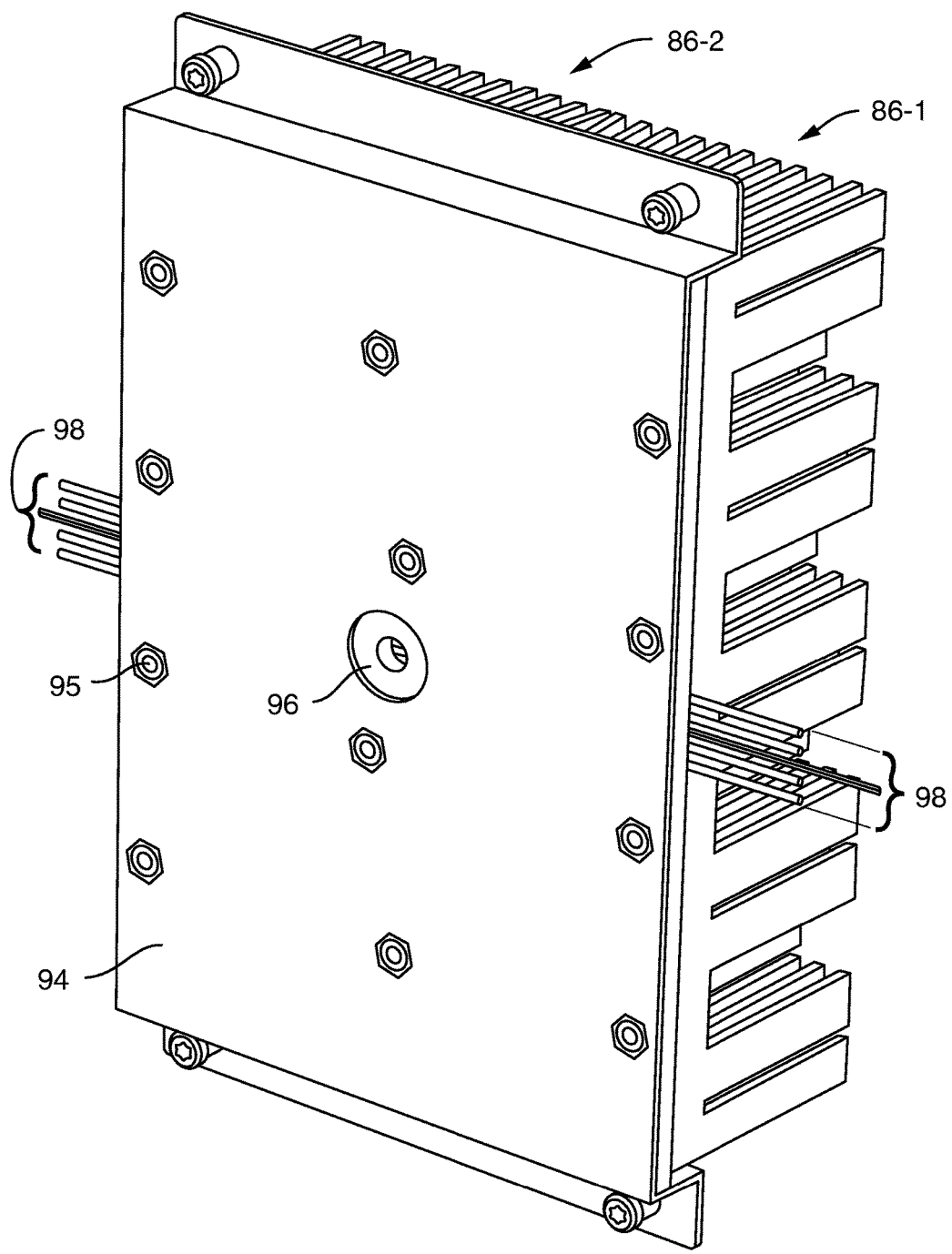
FIG. 11 is a rear view of the actively controlled heat exchanger system.

FIG. 11 shows a rear view of the actively controlled heat exchanger system 54 of FIG. 10 with openings 95 aligned with the through-holes 92 of the active heaters 86, and a center hole 96 for receiving a cable (not shown). The cable delivers the signals for controlling the operation of the heaters 86. Electrical wires 98 extend from both sides of the actively controlled heat exchanger system 54, emerging from between the active heaters 86 and the rear plate 94.

Figure 12:
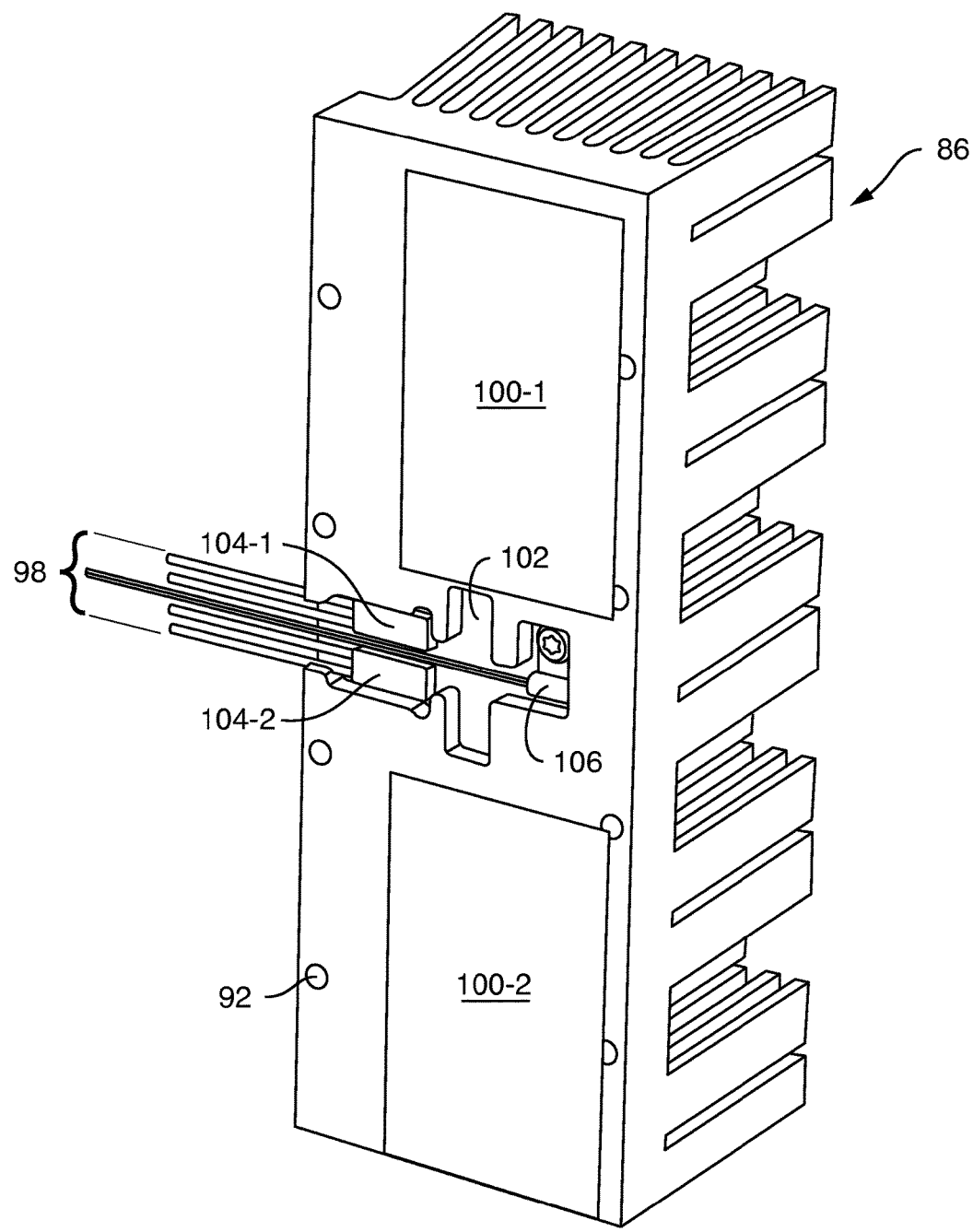
FIG. 12 is a rear view of an actively controlled heater.

FIG. 12 shows a rear view of an active heater 86 (detached from the rear plate 94). The active heater 86 has a pair of heater strips or pads 100-1, 100-2 and a cutout region 102. In one embodiment, the heater pads 100-1, 100-2 (generally, 100) are 2"×3" Kapton® Strip Heaters. Electrical wires (not shown) for running a current through the heater pads can pass through the cutout region 102. Splitting the active heater 86 allows control and safety components to be centered on the active heater within the cutout region 102. Disposed within the cutout region 102 is a pair of thermal safety switches 104-1, 104-2 (generally, 104) and a thermistor 106. The thermistor 106 measures the temperature of the active heater 86; the temperature controller 22 can use the measured temperature, for example, to monitor and control the air temperature (correlated to the heater temperature). The safety switches 104 operate to turn off a respective heater pad 100 in the event a current limit for the heater pad 100 is exceeded.

Figure 13:
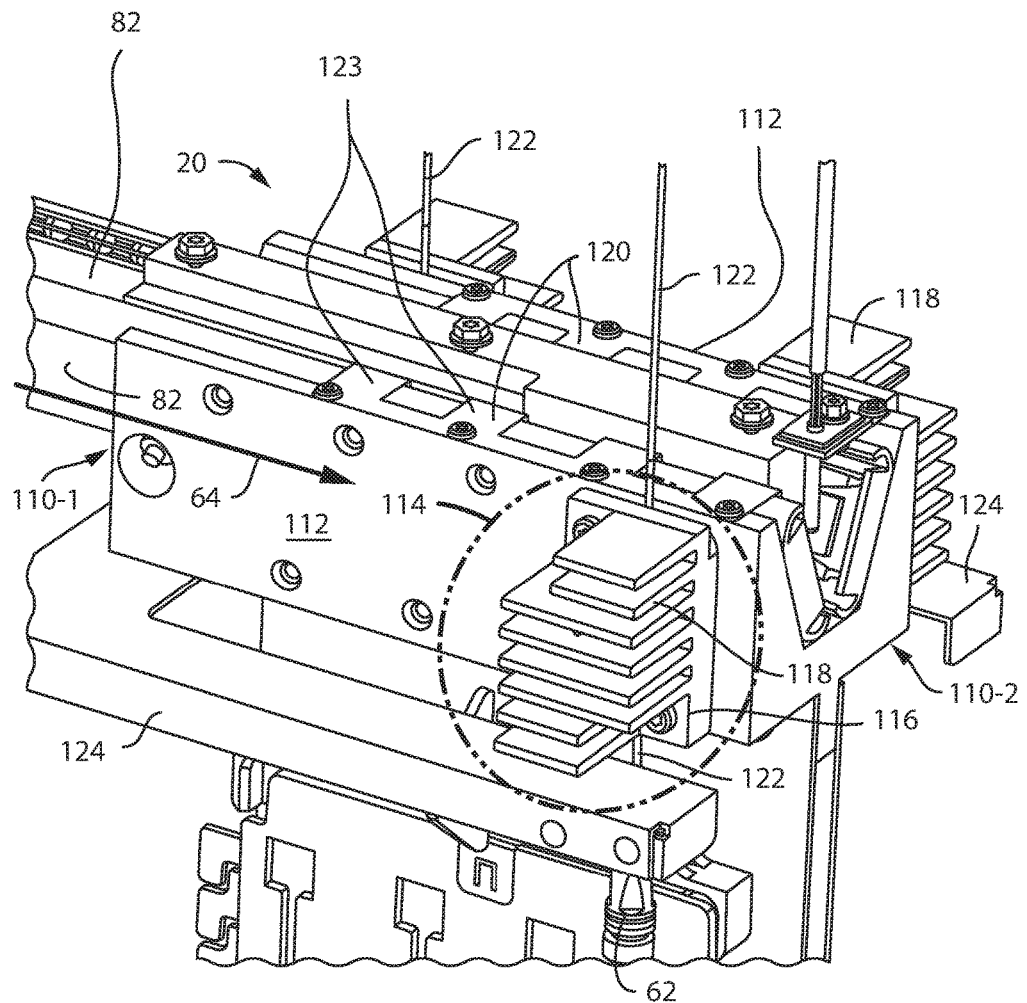
FIG. 13 is a side view of an embodiment of a passive pre-heater assembly for heating (or cooling) a fluid being delivered to a column within the column chamber.

FIG. 13 shows a side view of an embodiment of the passive pre-heater assembly 20 comprised of pair of passive pre-heater units 110-1, 110-2 (generally 110). Each passive pre-heater unit 110 includes a thermally conductive (e.g., aluminum) heat-spreading block 112 and one or more passive pre-heaters 114. The shown embodiment of the heat-spreading block 112 can have as many as four passive pre-heaters 114 mounted thereto; accordingly, the passive pre-heater assembly 20, having two heat-spreading blocks 112, can have as many as eight mounted passive pre-heaters 114. The passive pre-heater assembly 20 can be populated with all eights passive pre-heaters 114, even if all are not in use, to transfer heat to the heat-spreading block 112. Though not being used to heat fluid —they need not have a groove or be otherwise adapted to hold a tube —"dummy" pre-heaters 114 can still serve to transfer heat from the air to the heat-spreading block 112. By sharing the heat load among all eight passive pre-heaters 114, the heat transfer from ambient air to the heat-spreading block 112 occurs more efficiently than if the heat-spreading block 112 were populated with only those passive pre-heaters 114 in use. A lone pre-heater 114 may prove insufficient to achieve a desired performance level because of the thermal resistance between the flowing air and the pre-heater 114. An edge of the heat-spreading block has one or mounting flanges 123 adapted to slidably couple the heat-spreading block to the slider rail 82. The heat-spreading block 112 thus becomes the main source of heat for the pre-heaters 114, which the heat-spreading block 112 distributes across those passive pre-heaters 114. Each passive pre-heater 114 in use (connected to a column) draws heat from the heat-spreading block 112.

Each passive pre-heater 114 includes a thermally conductive base 116 and a plurality of heat sink extrusions (or, simply, fins) 118 integrally formed with or removably coupled to the base 116, for conductively exchanging heat with the 116 base. The fins 118 are horizontally arranged to align with the direction of the airflow (indicated by arrow 64) to present minimal resistance to the airflow, while exposing most of their surface area to facilitate convective heat exchange with the flowing air. Some fins 118 are narrower than other fins to make room for fasteners that mount the pre-heater 114 to the heat-spreading block 112. In one embodiment, the passive pre-heaters 114 are approximately 1.25" wide and 2.25" in height.

A fluidic tube 122 enters each passive pre-heater 114 in use from above and exits the passive pre-heater 114 from below. The tube 122 terminates at a column fitting 62 (also FIG. 3). In brief overview, the fins 118 draw heat from the air and conduct the heat to the base 116. Each passive pre-heater 114 in use draws heat from the base 116 and from the heat-spreading block 112, and transfers the heat to the fluid passing through the tube 122. The length of the tube 122 within the base 116 and the heat transfer area between the base 116 and the heat-spreading block 112 are designed to produce a fluid temperature that approximately equals the air temperature. Simulations show that the temperature of the heat-spreading block 112 comes to within 1° to 2° C. of the air temperature. A thermistor (not shown) can be placed in thermally conductive contact with the heat-spreading block 112 to obtain a measure of the temperature at the pre-heater assembly 20, which can be used as feedback for controlling the air temperature produced by the actively controlled heat exchanger system 54.

A U-shaped shelf 124 is disposed below the pre-heater units 110 to contain the airflow 64 in the general vicinity of the fins 118. A rail mount 120 slidably mounts the pre-heater units 110 to the slider rail 82. The pre-heater assembly 20 can slide in and out of the enclosure 16 to facilitate plumbing of the tubes 122.

One embodiment of a passive pre-heater 114 can have a cooling element (not shown), for example, a Peltier device or other thermoelectric cooling device, or liquid nitrogen, or liquid $CO_2$, adapted to cool the pre-heater 114. The cooling element can be adapted to cool rapidly the base 116 of the pre-heater 114 to a target sub-ambient temperature, thereby cooling the fluid passing through the tube 122. The temperature controller 22 (FIG. 1) can coordinate the cooling of the passive pre-heater 114 with the turning off or reducing the temperature produced by the actively controlled heat exchange system 54. In an embodiment having a powered cooling element, the passive pre-heater 114 is not entirely "passive"; the cooling element would be active, while the heating would be passive.

Figure 14:
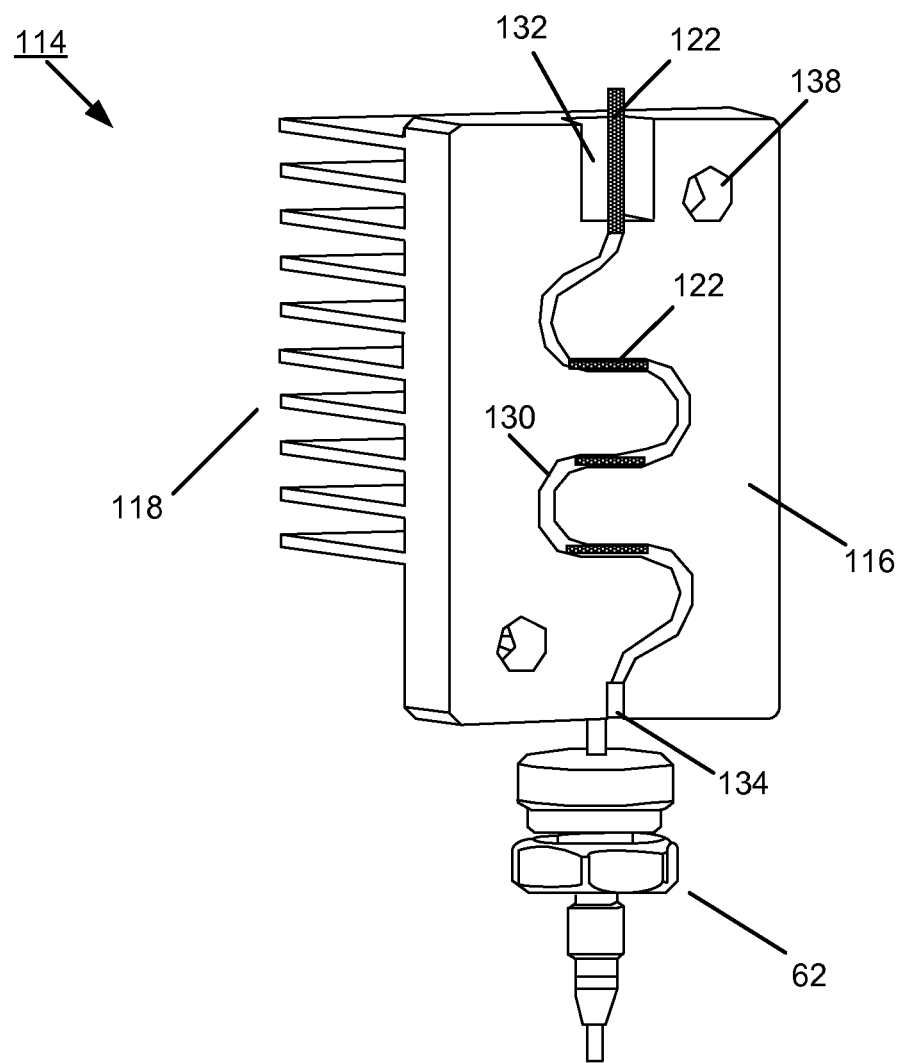
FIG. 14 is a rear view of an embodiment of a passive pre-heater in the passive pre-heater assembly.

FIG. 14 shows a rear view (i.e., the side that mounts to the heat-spreading block 112) of an embodiment of a passive pre-heater 114. The thermally conductive base 116 of the pre-heater 114 has a serpentine groove 130 that extends through the base 116 from an input port 132 to an output port 134. The groove 130 can range from approximately two inches to approximately three inches in length. Other groove lengths can be used without departing from the principles described herein. The groove 130 is on one side of the base 116 opposite the fins 118 and is sized to receive closely the fluidic tube 122. In one embodiment, the tube 122 has an inner diameter of approximately 0.005 inches. A thermal epoxy can be used to bond the tube 122 within the groove 130 and facilitate a heat transfer between the base 116 and the fluid passing through the tube 122. Other methods can be used to hold the tube 122 within the thermally conductive base 116; examples include, but are not limited to, the thermally conductive base 116 being molded over the tube 122, or solder can be used. The tube 122 terminates at a column fitting 62. Extending through the base 116 are holes 138 for receiving fasteners (e.g., captive screws that protrude) that secure the passive pre-heater 114 to the heat-spreading block 112. An elastomeric or graphite thermal gasket (not shown) is disposed between the base 116 of the pre-heater 114 and the heat-spreading block 112 and covers the groove 130. In general, the pre-heater 114 can be made of any thermally conductive material, for example, titanium, aluminum, or copper.

Other embodiments of the passive pre-heater 114 can lack the groove 130. For example, the tube 122 can be embedded in or cast in the thermally conductive base 116 (i.e., the base 116 is molded over the tube 122). Alternatively, the tube 122 can be sandwiched between two thermally conductive surfaces of the base 116 and the heat-spreading block 112, one or both of which surfaces are compliant to avoid pinching or crushing the tube 122.

While the invention has been shown and described with reference to specific preferred embodiments, it should be understood by those skilled in the art that various changes in form and detail may be made therein without departing from the spirit and scope of the invention as defined by the following claims. For example, other ducting patterns can be used to circulate heated air around the column chamber without departing from the principles described herein.

What is claimed is:

1. A passive column pre-heater assembly for use in a chromatographic system, comprising:
  a thermally conductive heat-spreading block; and
  a plurality of passive pre-heaters in thermally conductive communication with the heat-spreading block to exchange heat with the thermally conductive heat-spreading block, each pre-heater comprising:
    a thermally conductive base in thermal communication with the heat-spreading block; and
    a plurality of thermally conductive fins in thermal communication with the thermally conductive base of the pre-heater, the plurality of fins being adapted to exchange heat convectively with ambient air and conductively with the thermally conductive base of the pre-heater, and
  wherein a given one of the passive pre-heaters further comprises a tube in thermally conductive contact with the thermally conductive base of the given passive pre-heater, and wherein the thermally conductive heat-spreading block is configured to exchange heat with a fluid passing through the tube of the given passive pre-heater, wherein the given one of the plurality of passive pre-heaters achieves a transfer of heat from ambient air to the fluid within the tube without any active temperature control on the part of the pre-heater assembly.

2. The passive column pre-heater assembly of claim 1, wherein the given one of the passive pre-heaters further comprises a groove formed in the thermally conductive base of the given passive pre-heater, and wherein the tube is embedded within the groove, with an inlet end of the tube extending from one end of the groove, an outlet end of the tube extending from an opposite end of the groove, and the outlet end of the tube having a chromatography column fitting configured for coupling to a chromatography separation column.

3. The passive column pre-heater assembly of claim 2, wherein the tube is secured within the groove by a thermal epoxy.

4. The passive column pre-heater assembly of claim 1, further comprising a thermal gasket disposed between the thermally conductive base of each pre-heater and the thermally conductive heat-spreading block.

5. The passive column pre-heater assembly of claim 1, further comprising:
   a second thermally conductive heat-spreading block; and
   a second plurality of passive pre-heaters in thermally conductive communication with the second thermally conductive heat-spreading block configured to exchange heat therewith, each pre-heater of the second plurality of passive pre-heaters comprising:
      a thermally conductive base in thermal communication with the second heat-spreading block; and
      a plurality of thermally conductive fins in thermal communication with the thermally conductive base of that pre-heater of the second plurality of passive pre-heaters, each of the plurality of thermally conductive fins being adapted to exchange heat convectively with ambient air and conductively with the thermally conductive base of that pre-heater of the second plurality of passive pre-heaters.

6. The passive column pre-heater assembly of claim 5, wherein a given one of the second plurality of passive pre-heaters further comprises:
   a groove formed in the thermally conductive base of the given passive pre-heater of the second plurality of passive pre-heaters; and
   a tube embedded within the groove,
   wherein the tube is configured to receive a fluid such that the fluid passes through the tube of the given passive pre-heater of the second plurality of passive pre-heaters and exchanges heat with the second thermally conductive heat-spreading block.

7. The passive column pre-heater assembly of claim 5, wherein the thermally conductive heat-spreading blocks are in thermal communication with each other.

8. The passive column pre-heater assembly of claim 5, wherein the plurality of thermally conductive fins of each pre-heater of the second plurality of pre-heaters extend in an opposite direction from the plurality of thermally conductive fins of each pre-heater of the other plurality of pre-heaters.

9. The passive column pre-heater assembly of claim 5, wherein a section of the second heat-spreading block is spatially separated from and opposite of a corresponding section of the other heat-spreading block.

10. An apparatus, comprising:
   a column chamber adapted to hold one or more chromatography separation columns;
   a chromatography separation column disposed in the column chamber;
   a passive pre-heater assembly comprising:
      a thermally conductive heat-spreading block; and
      a plurality of passive pre-heaters in thermally conductive communication with the heat-spreading block configured to exchange heat with the thermally conductive heat-spreading block, each pre-heater comprising:
         a thermally conductive base in thermal communication with the heat-spreading block;
         a plurality of thermally conductive fins in thermal communication with the thermally conductive base,
   wherein a given one of the passive pre-heaters further comprises a tube in thermally conductive contact with the thermally conductive base of the given passive pre-heater, with one end of the tube in fluidic communication with the chromatography separation column in the column chamber such that the tube is configured to convey a fluid to the chromatography separation column, wherein the given one of the plurality of passive pre-heaters achieves a transfer of heat from ambient air to the fluid within the tube without any active temperature control on the part of the pre-heater assembly; and
   an air mover configured to move a flow of air across the plurality of thermally conductive fins of each of the passive pre-heaters such that (i) each of plurality of thermally conductive fins exchanges heat convectively with the flow of air and conductively with the thermally conductive base of that pre-heater, (ii) the thermally conductive base of each passive pre-heater exchanges heat conductively with the heat-spreading block, and (iii) the heat-spreading block exchanges heat conductively with the fluid conveyed by the tube.

11. The apparatus of claim 10, further comprising a shelf disposed near the heat-spreading block to contain the flow of air near the plurality of thermally conductive fins of the plurality of passive pre-heaters.

12. The apparatus of claim 10, wherein the plurality of thermally conductive fins of each passive pre-heater is aerodynamically oriented with a direction of the flow of air.

13. The apparatus of claim 10, further comprising a sliding rail coupled to the passive pre-heater assembly, the sliding rail being adapted to slide into and out of the enclosure with the passive pre-heater assembly coupled thereto.

14. The apparatus of claim 13, wherein an edge of the heat-spreading block has one or mounting flanges adapted to slidably couple the heat-spreading block to the sliding rail.

15. The apparatus of claim 10, further comprising a thermal gasket disposed between the thermally conductive base of each pre-heater and the thermally conductive heat-spreading block.

16. The column-conditioning enclosure of claim 10, further comprising:
   a second thermally conductive heat-spreading block; and
   a second plurality of passive pre-heaters in thermally conductive communication with the second heat-spreading block to exchange heat therewith, each pre-heater of the second plurality of passive pre-heaters comprising:
      a thermally conductive base in thermal communication with the second heat-spreading block; and
      a plurality of thermally conductive fins in thermal communication with the thermally conductive base of the pre-heater, each of the plurality of thermally conductive fins being adapted to exchange heat convectively with the flow of air and conductively with the thermally conductive base of that pre-heater of the second plurality of passive pre-heaters.

17. The column-conditioning enclosure of claim 16, wherein a given pre-heater of the second plurality of passive pre-heaters further comprises:
   a groove formed in the thermally conductive base of the given passive pre-heater of the second plurality of passive pre-heaters; and a tube embedded within that groove, one end of the tube being in fluidic communication with a second given column of the one or more chromatography separation columns in the column chamber, the tube conveying a fluid to the second given column, wherein (i) each of plurality of thermally conductive fins of the second plurality of pre-heaters exchanges heat convectively with the flow of air and conductively with the thermally conductive base of that pre-heater, (ii) the thermally conductive base of each of the second plurality of passive pre-heaters exchanges heat conductively with the second heat-spreading block, and (iii) the second heat-spreading block exchanges heat conductively with the fluid conveyed by the tube in the groove of the given pre-heater of the second plurality of passive pre-heaters.

18. The column-conditioning enclosure of claim 16, wherein the thermally conductive heat-spreading blocks are in thermal communication with each other.

19. The column-conditioning enclosure of claim 16, wherein the plurality of thermally conductive fins of each pre-heater of the second plurality of pre-heaters extend in an opposite direction from the plurality of thermally conductive fins of each pre-heater of the other plurality of pre-heaters.

20. The column-conditioning enclosure of claim 16, wherein a section of the second heat-spreading block is spatially separated from and opposite of a corresponding section of the other heat-spreading block.

21. A method for pre-heating a fluid being delivered to a chromatography separation column, the method comprising:
thermally coupling a plurality of passive pre-heaters to a thermally conductive heat-spreading block;
configuring a given pre-heater of the plurality of passive pre-heaters with a tube and a column fitting for conveying a fluid to a chromatography separation column;
convectively transferring heat from ambient air to each pre-heater of the plurality of passive pre-heaters;
conductively transferring heat from each of the plurality of passive pre-heaters to the thermally conductive heat-spreading block;
conductively transferring heat from the heat-spreading block to the fluid passing through the tube in the given pre-heater of the passive pre-heaters;
achieving, with the given preheater of the plurality of passive pre-heaters, a transfer of heat from ambient air to the fluid within the tube without any active temperature control on the part of the plurality of passive pre-heaters or the thermally conductive heat spreading block; and
delivering pre-heated fluid from within the tube to the chromatography separation column.

22. A passive column pre-heater for use in a chromatographic system, comprising: a thermally conductive base; a plurality of parallel, thermally conductive fins in thermal communication with the thermally conductive base, the plurality of fins exchanging heat convectively with ambient air and conductively with the thermally conductive base; and a tube in thermally conductive contact with the thermally conductive base for effectuating an exchange of heat between the thermally conductive base and a fluid passing through the tube, and wherein the thermally conductive base is configured to exchange heat with a fluid passing through the tube of the passive column pre-heater, wherein the passive column pre-heater is configured to achieve a transfer of heat from ambient air to the fluid within the tube without any active temperature control on the passive column pre-heater.

23. The passive column pre-heater of claim 22, wherein the thermally conductive base has a groove formed therein, and the tube is embedded within the groove, the tube further comprising: an inlet end extending from one end of the groove; and an outlet end extending from an opposite end of the groove, the outlet end of the tube having a chromatography column fitting for coupling to a chromatography separation column.

24. The passive column pre-heater of claim 23, wherein the groove is serpentine within the thermally conductive base.

25. The passive column pre-heater of claim 22, wherein the tube is secured within the groove by a thermal epoxy.

26. The passive column pre-heater of claim 22, further comprising a cooling element thermally coupled to the thermally conductive base for cooling the thermally conductive base and effectuating an exchange of heat from the fluid passing through the tube in the groove and the thermally conductive base.

27. The passive column pre-heater of claim 23, further comprising a thermal gasket disposed on the thermally conductive base covering the groove.

28. The passive column pre-heater of claim 23, wherein the groove is approximately two to three inches in length.

29. The passive column pre-heater of claim 22, wherein the tube has an inner diameter of approximately 0.005 inches.

30. The passive column pre-heater of claim 22, wherein the thermally conductive base has a width of approximately 1 inch and a height of approximately 2 inches.

* * * * *